US011107371B2

(12) United States Patent
Salvino (10) Patent No.: US 11,107,371 B2
(45) Date of Patent: Aug. 31, 2021

(54) RIB TRAINING ASSEMBLY

(71) Applicant: Chris Salvino, Scottsdale, AZ (US)

(72) Inventor: Chris Salvino, Scottsdale, AZ (US)

(73) Assignee: Sharp Medical Products—Chest Tube, LLC., Scottsdale, AZ (US)

( * ) Notice: Subject to any disclaimer, the term of this patent is extended or adjusted under 35 U.S.C. 154(b) by 0 days.

(21) Appl. No.: 15/930,385

(22) Filed: May 12, 2020

(65) Prior Publication Data

US 2020/0372832 A1   Nov. 26, 2020

Related U.S. Application Data

(60) Provisional application No. 62/852,474, filed on May 24, 2019.

(51) Int. Cl.
*G09B 23/30* (2006.01)
*A61B 34/10* (2016.01)

(52) U.S. Cl.
CPC .............. *G09B 23/30* (2013.01); *A61B 34/10* (2016.02); *A61B 2034/105* (2016.02)

(58) Field of Classification Search
CPC ......... G09B 23/28; G09B 23/30; G09B 23/34
USPC ....................................... 434/262, 267, 272
See application file for complete search history.

(56) References Cited

U.S. PATENT DOCUMENTS

| 5,803,746 | A * | 9/1998 | Barrie ................... G09B 23/30 434/262 |
| 5,947,743 | A * | 9/1999 | Hasson ................ G09B 23/286 434/262 |
| 6,780,016 | B1 | 8/2004 | Toly |
| 8,556,635 | B2 * | 10/2013 | Toly ..................... G09B 23/285 434/272 |
| 8,647,124 | B2 | 2/2014 | Bardsley et al. |
| 8,801,438 | B2 | 8/2014 | Sakezles |
| 9,922,579 | B2 * | 3/2018 | Black ..................... G09B 23/34 |
| 10,255,829 | B2 * | 4/2019 | Lee ....................... G09B 23/285 |
| 10,354,556 | B2 * | 7/2019 | Hofstetter .............. G09B 23/30 |
| 10,410,542 | B1 | 9/2019 | Stone et al. |
| 10,535,281 | B2 | 1/2020 | Breslin et al. |
| 10,679,520 | B2 * | 6/2020 | Hofstetter .............. G09B 23/30 |
| 10,796,606 | B2 * | 10/2020 | Felsinger .............. G09B 23/30 |
| 2008/0064017 | A1 * | 3/2008 | Grundmeyer, III .... G09B 23/28 434/262 |
| 2014/0349265 | A1 * | 11/2014 | Park ...................... G09B 23/32 434/272 |

(Continued)

*Primary Examiner* — Kurt Fernstrom (74) *Attorney, Agent, or Firm* — Kenneth Altshuler (57) ABSTRACT

A rib retention training assembly that is beneficial for training and practicing chest tube insertion and other invasive rib surgical procedures is envisioned to incorporate a portion of an animal rib cage covered by a synthetic sheet of human-like skin. One embodiment contemplates an apparatus comprising three framed plates each with an aperture in the center, much like a picture frame. When assembled, the synthetic sheet of human-like skin is sandwiched between a first outer framed plate and a center framed plate such that the synthetic sheet is covering the respective apertures, and the portion of the animal rib cage is sandwiched between the center frame plate and a second outer framed plate such that the rib cage is covering the respective apertures. This assembly provides a chest prop with a realistic feel for surgical simulations.

20 Claims, 6 Drawing Sheets

(56) References Cited

U.S. PATENT DOCUMENTS

2016/0071437 A1    3/2016  Hoke et al.
2020/0160752 A1*   5/2020  Lin ........................ G09B 23/34

* cited by examiner

RIB TRAINING ASSEMBLY

CROSS-REFERENCE TO RELATED APPLICATIONS

This application claims priority to and the benefit of U.S. Provisional Patent Application No. 62/852,474 entitled: Rib Training Assembly, filed on May 24, 2019.

FIELD OF THE INVENTION

The present embodiments are directed to a rib retention training assembly beneficial for training and practicing chest tube insertion and other invasive rib surgical procedures.

DESCRIPTION OF RELATED ART

The lungs are surrounded by a pleural sac made up of two membranes, the visceral and parietal pleurae. The parietal pleura lines the thoracic wall, and the visceral pleura surrounds the lung. The pleural space is a potential space between these two layers of pleurae. It contains a thin layer of serous pleural fluid that provides lubrication for the pleurae and allows the layers of pleurae to smoothly slide over each other during respiration. In abnormal circumstances the pleural space can fill with air and certain types of fluids not normally present requiring drainage.

In the industrialized world, trauma is the leading cause of death in males under the age of forty. In the United States, chest injuries are responsible for one-fourth of all trauma deaths. Many of these fatalities could be prevented by early recognition of the injury followed by prompt management. Some traumatic chest injuries require quick placement of chest tubes to drain out air and/or fluids (such as blood) from the chest cavity.

Several techniques are currently used to insert a chest tube, each of which involves a relatively lengthy manual procedure that requires knowledge and experience. The most common technique involves surgical preparation and draping at the site of the tube insertion (usually at the nipple level-fifth intercostal space, anterior to the mid-axillary line on the affected side), administering local anesthesia to the insertion site, and making a 2-4 cm vertical incision. A clamp is inserted through the incision and spread thereby tearing muscle and tissue until a tract large enough to accept a finger. Next, the parietal pleura is punctured, which can be accomplished with the tip of a clamp. On occasion, the surgeon places a gloved finger into the incision to confirm the presence of a free pleural space locally. Next, the proximal end of a chest tube is advanced through the incision into the pleural space. As the chest tube is inserted, it is sometimes directed posteriorly and superiorly towards the apex of the lung or elsewhere in the chest cavity. The goal is for the chest tube to drain the pleural space of both air and/or fluids.

Training personnel to insert a chest tube using standard techniques is often done with an expensive manikin and in some cases on a living person in an emergency situation. With respect to the manikin, there are only so many practice insertions before the manikin either needs to be refurbished or is disposed of. Also, most surgeons complain that manikins do not have the feel of a real person because the tissue is typically latex and rubber. In cases where a trainee assists a surgeon or otherwise experienced operator in performing chest tube insertions on a living traumatized human patient, real and actionable experience is gained but potentially at the expense of the human patient.

It is to innovations related to this subject matter that the claimed invention is generally directed.

SUMMARY OF THE INVENTION

The present embodiments are directed to a rib retention training assembly beneficial for training and practicing chest tube insertion and other invasive rib surgical procedures.

Certain embodiments of the present invention contemplate a chest tube trainer device comprising: a first plate with a first aperture in the first plate; a second plate with the second aperture and the second plate; a third plate with a third aperture in the third plate; a synthetic sheet of human-like skin clamped between the first plate and the second plate, the synthetic sheet covering the first aperture and the second aperture, the first aperture and the second aperture overlap; and a portion of a processed animal rib cage clamped between the second plate and the third plate, the portion comprising section of at least two adjacent animal ribs, the second aperture and the third aperture overlap.

Yet other certain embodiments of the present invention contemplate a rib retention training apparatus comprising: a first plate with a first aperture in the first plate; a second plate with the second aperture and the second plate; a clamping means adapted to clamped the first plate to the second plate with the first aperture and the second aperture overlapping, a means for retaining a synthetic sheet of human-like skin in a fixed position over the first aperture, the first plate and the second plate configured to compress and fixedly retain a portion of an animal rib cage when the first plate and the second plate are clamped together, the portion covering the first and the second aperture.

While other certain embodiments of the present invention contemplate method for assembling a rib retention training apparatus, the method comprising: providing a first frame with a first aperture in the first frame, a second frame with a second aperture in the second frame, and a third frame with a third aperture in the third frame; disposing a portion of an animal rib cage between the second frame and the third frame and disposing a synthetic sheet of human-like skin between the second frame and the first frame, the animal rib cage essentially covering the third aperture and the synthetic sheet of human-like skin essentially covering the second aperture, the apertures essentially overlapping; clamping the frames together to compress the synthetic sheet of human-like skin and the portion of the animal rib cage in an immobile arrangement; and providing space between the third frame and any surface opposing the third frame.

DETAILED DESCRIPTION

Initially, this disclosure is by way of example only, not by limitation. Thus, although the instrumentalities described herein are for the convenience of explanation, shown and described with respect to exemplary embodiments, it will be appreciated that the principles herein may be applied equally in other types of situations involving similar uses of a rib retention training apparatus. In what follows, similar or identical structures may (and may not) be identified using identical callouts.

Certain embodiments of the present invention generally relate to an assembly that provides a non-human surgical chest prop that has a realistic feel for chest tube insertion simulations and other related surgical simulations/training. In certain embodiments, a synthetic sheet of human-like skin is overlaid on a portion of an animal rib cage, such as a goat, pig, or other animal sized similar to a particular human body type (fat, thickness, rib spacing, etc.). synthetic human skin can be provided by any number of manufacturers and range from rubber, silicone to silicone/rubber impregnated fabric. The portion of the animal rib cage is devoid of epidermis (outer skin that would normally cover the animals rib cage) because animal skin is generally difficult to cut in relation to human skin. In other words, a portion of skinless animal ribs can be easily obtained from a meat market. Some embodiments contemplate the portion of an animal rib cage sized to include at least two adjacent ribs that are at least 3 inches long (that is cut in length to at least 3 inches long). In some other embodiments, a portion of animal rib cage being greater than a five inch by five inch square is envisioned. The synthetic sheet of human-like skin is at least the size of the portion of the animal rib cage in order to reasonably cover the portion of the animal rib cage that is stripped of the animal's skin. Other embodiments envision the synthetic sheet of human-like skin having a perimeter being approximately one or more inches larger than the perimeter of the portion of the animal rib cage.

Figure 1:
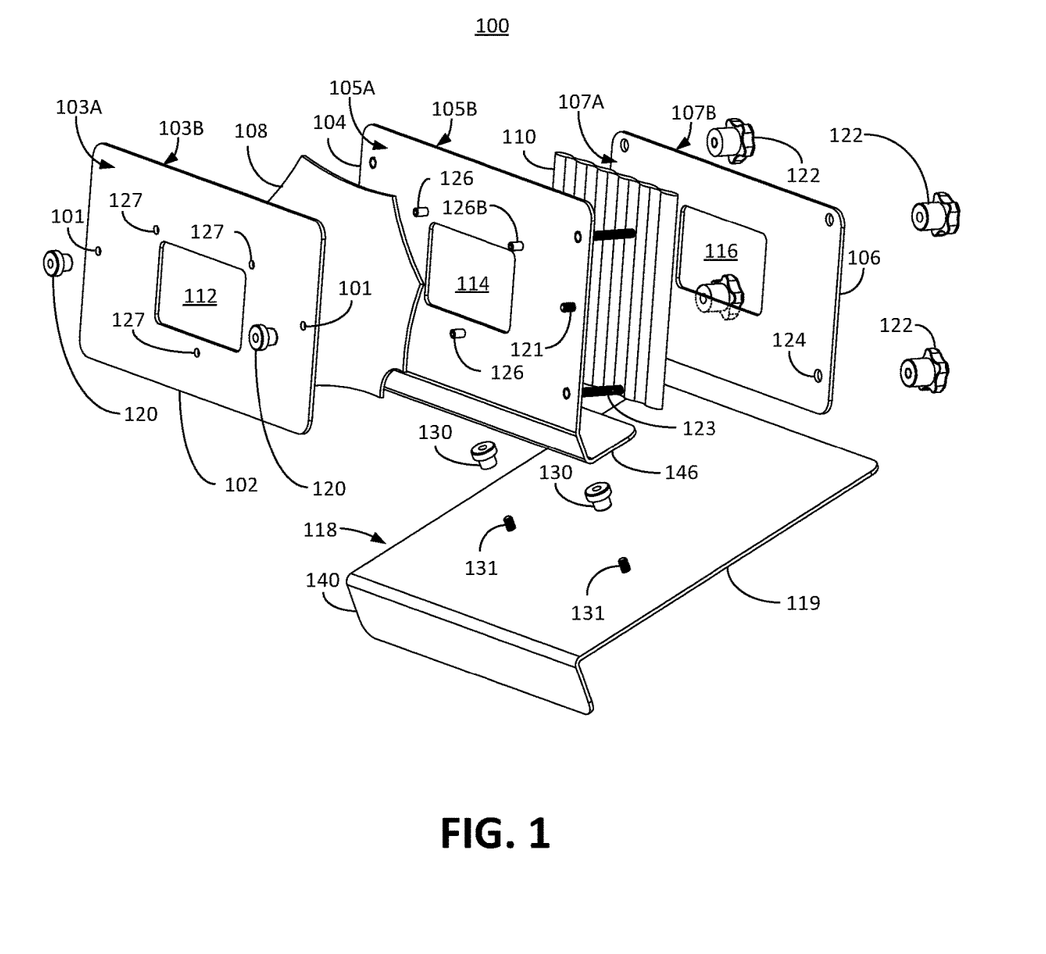
FIG. 1 illustratively depicts a line drawing of an exploded view of a rib retention training apparatus consistent with embodiments of the present invention.

In one arrangement, one surface of the portion of the animal rib cage is overlaid with an appropriately sized synthetic sheet of human-like skin clamped together between two plates in a fixed relationship. Each plate has an aperture that exposes the synthetic sheet and rib cage portion. Certain embodiments envision the plates being shaped similar to a picture frame. The apertures can be aligned so that tools can penetrate the animal rib cage through the synthetic sheet of human-like skin without obstruction from the plates. In this way, tools and tubes can penetrate through the rib cage through the apertures without obstruction from the plates. Other embodiments envision a middle plate shaped like the other two plates that is interposed between the synthetic sheet and rib cage portion, as shown in FIG. 1. In this arrangement, the three apertures are essentially aligned, or otherwise superimposed, to provide a pathway for a tool to enter in through the synthetic sheet of human-like skin and out the portion of the animal rib cage without obstruction from the plates. The plates can be made of metal, plastic or some other rigid material. Depending on the application, the apertures are envisioned to be greater than 2 inches by two inches, but could be smaller or larger as needed. Certain other embodiments envision the apertures being a square of at least 5 inches by 5 inches wide. Other certain embodiments envision a rectangle, circular, elliptical, or some other shape.

FIG. 1 illustratively depicts a line drawing of an exploded view of a rib retention training apparatus 100 consistent with embodiments of the present invention. Fundamentally, the embodiment includes an animal rib cage 110 and a synthetic sheet of human-like skin 108 clamped between three framed plates 102, 104 and 106. Essentially in the center of each framed plate 102, 104 and 106 is an aperture through which a surgical trainee can practice inserting a chest tube or related instruments.

More specifically, FIG. 1 depicts a synthetic sheet of human-like skin 108 located between the first framed plate 102 and the second framed plate 104, and more specifically in contact with the back side 103B of the first framed plate 102 and the front side 105A of the second framed plate 104. The first framed plate 102 and the second framed plate 104 each comprise an aperture 112 and 114 (or unobstructed opening), respectively, that passes completely through the plate creating a frame, similar to a picture frame. The apertures 112 and 114 are rectangular in shape. The first framed plate 102 is configured to be clamped to the framed second plate 104 to compress and otherwise lock the synthetic sheet of human-like skin 102 in an immobile configuration that covers the first aperture 112 and the second aperture 114. Means for clamping the first framed plate to the second framed plate can be accomplished with bolts, quick release, clamps, clasps, locks and other clamping hardware known to those skilled in the art. Certain embodiments envision the synthetic sheet of human-like skin 108 being locked in place mechanically by a plurality of retention fixtures, such as the pin 126 and slot 127 arrangement comprised by the first and second framed plates 102 and 104. In the present embodiment there are three pins 126 that slidingly engage mating slots/holes 127. Certain other embodiments envision clamps, different slot configurations, textured surfaces, ridges or other mechanical features that will prevent the synthetic sheet of human-like skin 108 from sliding from between the clamped plates 102 and 104.

The first and second framed plates 102 and 104 are clamped together by way of a knurled nut 120 and bolt 121 relationship. The knurled nuts 120 are configured to screw into mating receiving short bolts 121 that extend from the front surface 105A of the second framed plate 104 and through the receiving bolt holes 101 shown passing through the front surface 103A of the first framed plate 102. The short bolts 121 are so termed because they need only be long enough to compress the synthetic human-like skin 108 when the knurled nuts 120 are twisted by hand until tightly against the first plate 102. Certain embodiments envision the synthetic human-like skin 108 being stretched taut over the first aperture 112 or the second aperture 114 (depending on perspective) to otherwise block the passageway created by the first aperture 112 and 114.

As depicted in the present embodiment of FIG. 1, a portion of an animal rib cage 110 is configured to be sandwiched between the second framed plate 104 and the third framed plate 106 whereby the portion of the animal rib cage 110 is intended to be compressed and locked into place between the back surface of the second framed plate 105B and the front surface of the third framed plate 107A. Like the first and second framed plates 102 and 104, the third framed plate 106 also possesses a rectangular shaped aperture 116. Four long bolts 123 extend from the back side 105B of the second framed plate 104 and are configured to pass through receiving bolt holes 124 in the third framed plate 106 where they can engage finger nuts 122 from the back side of the third plate 107B. The finger nuts 122 can be tightened by hand around a long bolts 123 when engaged in a mating/cooperating relationship to compress the portion of the animal rib cage 110 in a fixed relationship between the second and third framed plates 104 and 106. The long bolts 123 are so termed because they need to accommodate the thickness of the portion of the animal rib cage 110. Certain embodiments envision ridges, a textured surface, spikes, or other locking features on the back surface 105B of the second framed plate 104 and/or the front surface 107A a third framed plate 106 to improve holding (or otherwise prevent sliding) of the portion of the animal rib cage 110 fixedly in place when the two framed plates 104 and 106 are clamped together. In the present embodiment, the first, second and third apertures 112, 114 and 116, respectively, are superimposed when connected and aligned and essentially form a common passageway in the absence of the synthetic human-like skin 108 and the portion of the animal rib cage 110. The common passageway facilitates a medical trainee to cut an incision through the synthetic human-like skin 108 and through the portion of the animal rib cage 110 that is sized to accommodate a chest tube, for example, in order to practice the surgery associated with inserting a chest tube. The first, the second and third framed plates 102, 104 and 106 keep the synthetic human-like skin 108 and the portion of the animal rib cage 110 immobilized for the training incision. Certain embodiments envision the portion of the animal rib cage 110 being at least part of two adjacent ribs connected through muscle and tissue, such as a 5 inch slab of ribs comprising rib #3 connected with rib #4 (and rib #5, etc.). In the present configuration, FIG. 1 illustratively depicts the portion of the animal rib cage 110 comprising six adjacent and connected pieces of rib.

Certain other embodiments envision the three framed plates 102, 104 and 106 being rigidly attached to a base 118 at an angle that is greater than horizontal when the platform 119 is referenced on a horizontal plane. In the present embodiment, a phalange 146 is formed from the second framed plate 104 where it can be attached with a nut 130 and bolt relationship 131 to the plate 118. In this way, the first, second and third apertures 112, 114 and 116, respectively, are not blocked by a surface, such as table surface, thereby providing space for a medical trainee to insert a chest tube or other device through the synthetic human-like skin 108 and the portion of the animal rib cage 110 without being obstructed at the back side of the third plate 107B. Some embodiments contemplate the space having a distance being greater than one inch, while others contemplate the distance being greater than two inches. The base 118 can be further tilted by a lip 125, as shown. Other embodiments envision any tilting angle of the three framed plates 102, 104 and 106 being solely accomplished by angling the base 118 by increasing the size of the lip 140. A skilled artisan will appreciate that tilting the base 118 via a lip 140 is merely a species for a broader tilting concept that can include a wedge shaped base, adjustable feet, etc.

Figure 2:
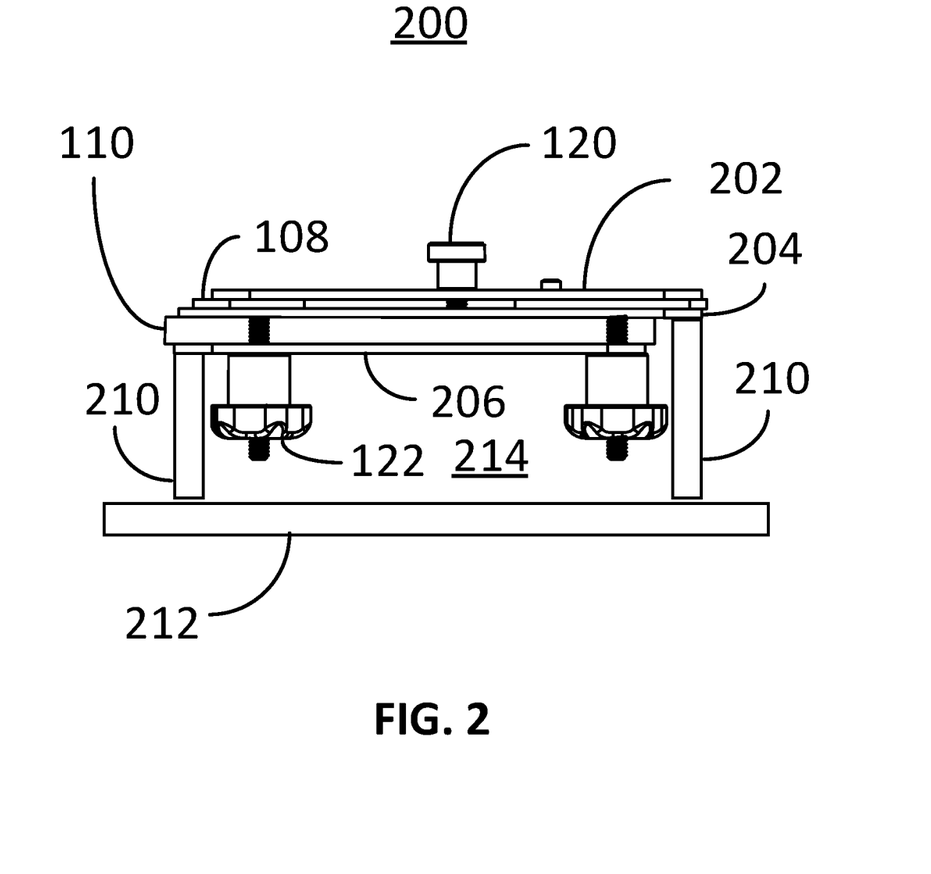
FIG. 2 illustratively depicts a side view line drawing of an optional embodiment of a rib retention training apparatus assembly consistent with embodiments of the present invention.

FIG. 2 illustratively depicts a line drawing of an optional embodiment of a rib retention training apparatus assembly 200 consistent with embodiments of the present invention. The three framed plates 202, 204 and 206 are spaced away from a surface such as a table surface 212 by spacers 210 to accommodate a medical trainee to insert a chest tube or other device through synthetic human-like skin 108 and a portion of an animal rib cage 110 without being obstructed (due to the working space 214) at the back side of the third plate 207B. In other words, the tip of a tool or chest tube can freely enter in working space 214 without obstruction.

Figure 3:
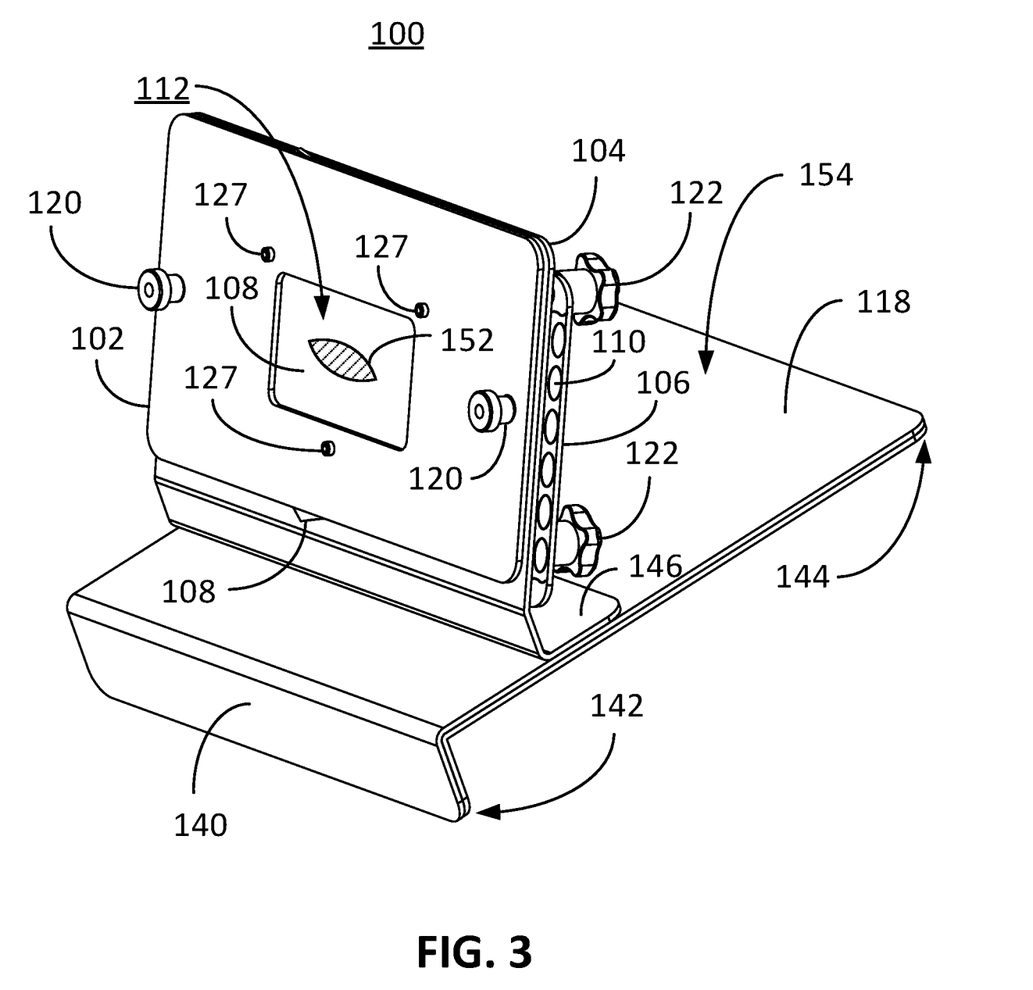
FIG. 3 illustratively depicts an isometric line drawing of the rib retention training apparatus of FIG. 1 assembled and compressing the synthetic human-like skin and the portion of the animal rib cage consistent with embodiments of the present invention.

FIG. 3 illustratively depicts a line drawing of the rib retention training apparatus 100 of FIG. 1 assembled and compressing the synthetic human-like skin 108 and the portion of the animal rib cage 110 consistent with embodiments of the present invention. As shown, an incision 152 is made through the synthetic human-like skin 108 that is clamped between the first framed plate 102 and the second framed plate 104. The combination of the synthetic human-like skin 108 coupled in this way against the portion of the animal rib cage 110 closely simulates the texture and consistency of a human rib cage and human skin. As is further shown, the relationship with the three framed plates 102, 104 and 106 to a base 118 at an angle that is greater than horizontal when the base 118 is referenced on a horizontal plane provides a working region/space 154 to accommodate a chest tube or some other tool that is made to penetrate through the portion of the animal rib cage 110 (the ribs are depicted by the ellipses) and out the other side into the working region/space 154. The base 118 is adapted to rest on a surface or table at locations 142 and 144 of the base 118. In the present embodiment, there is a base lip 140 that tips the front surface of the first framed plate 103A to better accommodate making the incision 152 and inserting a chest tube or other tool (not shown) through the incision and into the working region/space 154. The base lip 140 is a bend in the sheet metal, which in certain embodiments envisions the plates 202, 204 and 206 and the base 118 being made of the same gauge sheet metal. Other certain embodiments envision the plates 202, 204 and 206 and the base 118 being made from sheets of plastic or other rigid materials.

Figure 4:
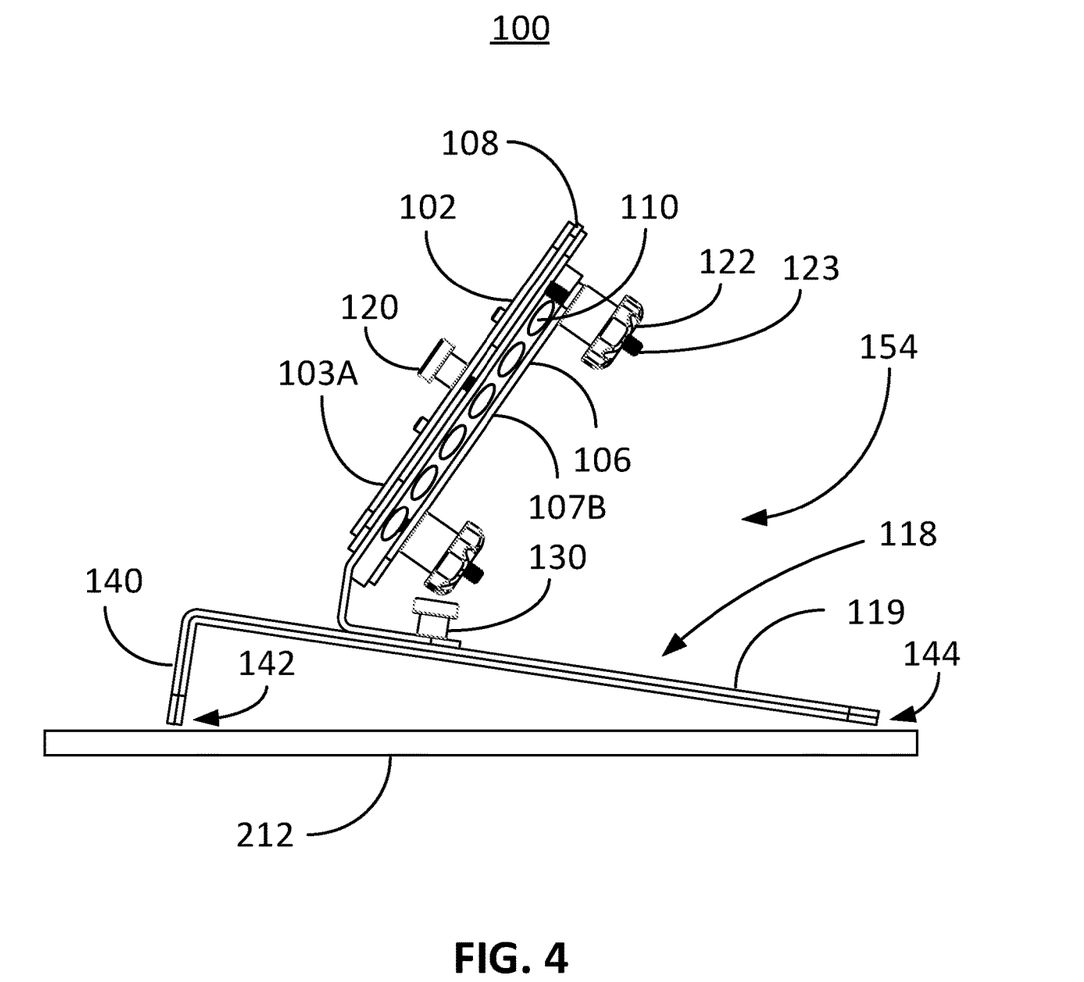
FIG. 4 illustratively depicts a side view line drawing of the rib retention training apparatus of FIG. 1 assembled and compressing the synthetic human-like skin and the portion of the animal rib cage consistent with embodiments of the present invention.

FIG. 4 illustratively depicts a side view line drawing of the rib retention training apparatus 100 of FIG. 1 assembled and compressing the synthetic human-like skin 108 and the portion of the animal rib cage 110 (the ellipses represent the cross-sectional cut rib bones) consistent with embodiments of the present invention. As shown, the three framed plates 102, 104 and 106 are rigidly attached to a base 118 at an angle that is greater than horizontal when the platform 119 is referenced on a horizontal plane, which is a table top 212 in this example. The base 118 is resting on the tabletop 212 at points 142 and 144. The lip 140 tilts the working surface of the front face of the first framed plate 103A so that a medical trainee can easily cut through the synthetic human-like skin 108 and through the animal rib cage 110. As also shown, the working region/space 154 has ample room to thread a chest tube (not shown) or other tool through an incision made in the synthetic human-like skin 108 and rib cage 110 to pass through the skin 108 and rib cage 110.

Figure 5:
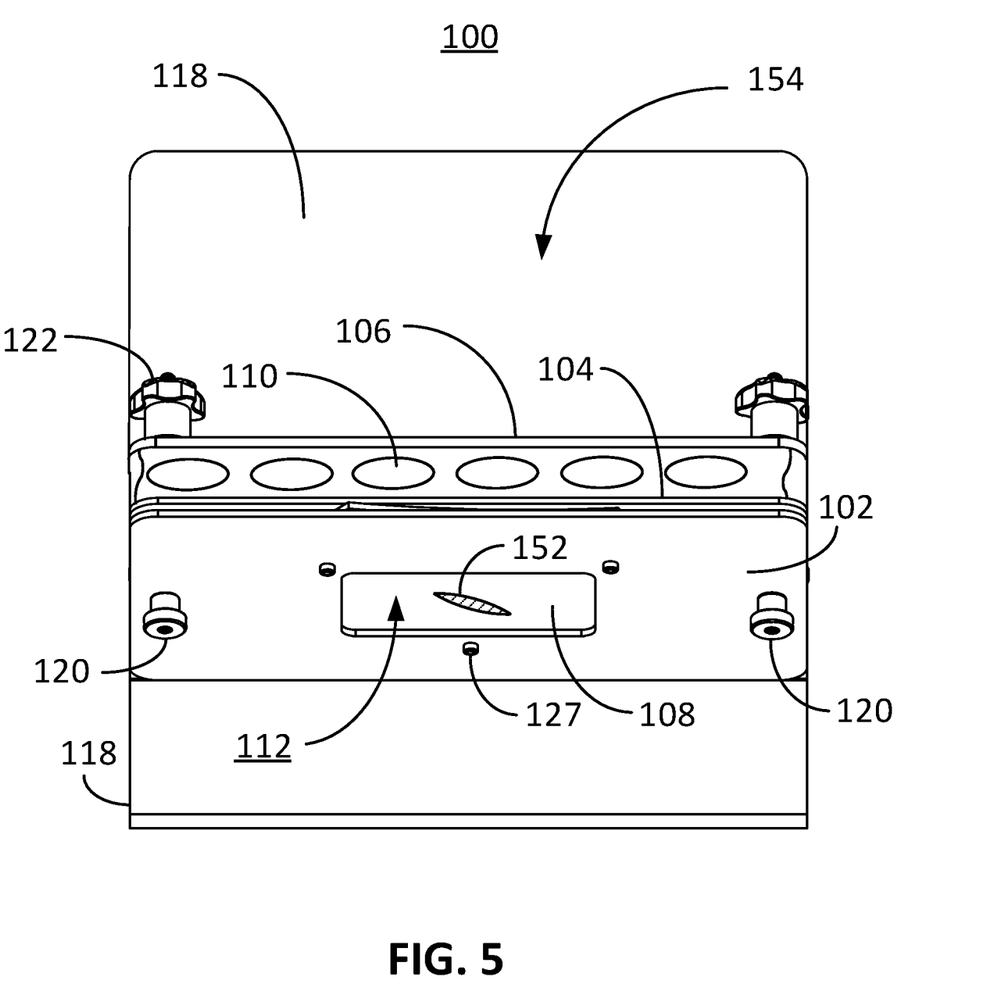
FIG. 5 illustratively depicts a top view line drawing of the rib retention training apparatus of FIG. 1 assembled and compressing the synthetic human-like skin and the portion of the animal rib cage consistent with embodiments of the present invention.

FIG. 5 illustratively depicts a top view line drawing of the rib retention training apparatus 100 of FIG. 1 assembled and compressing the synthetic human-like skin 108 and the portion of the animal rib cage 110 (the ellipses represent the cross-sectional cut rib bones) consistent with embodiments of the present invention. As shown, the three framed plates 102, 104 and 106 are rigidly attached to a base 118 at an angle that is greater than horizontal when the platform 119 is referenced on a horizontal plane. The first framed plate 102 is tilted so that a medical trainee can easily cut through the synthetic human-like skin 108 and through the animal rib cage 110, as shown by the incision 152 in the first aperture 112. Also as shown, the working region/space 154 provides ample space to thread a chest tube (not shown) or other tool through an incision made in the synthetic human-like skin 108 and rib cage 110.

Figure 6:
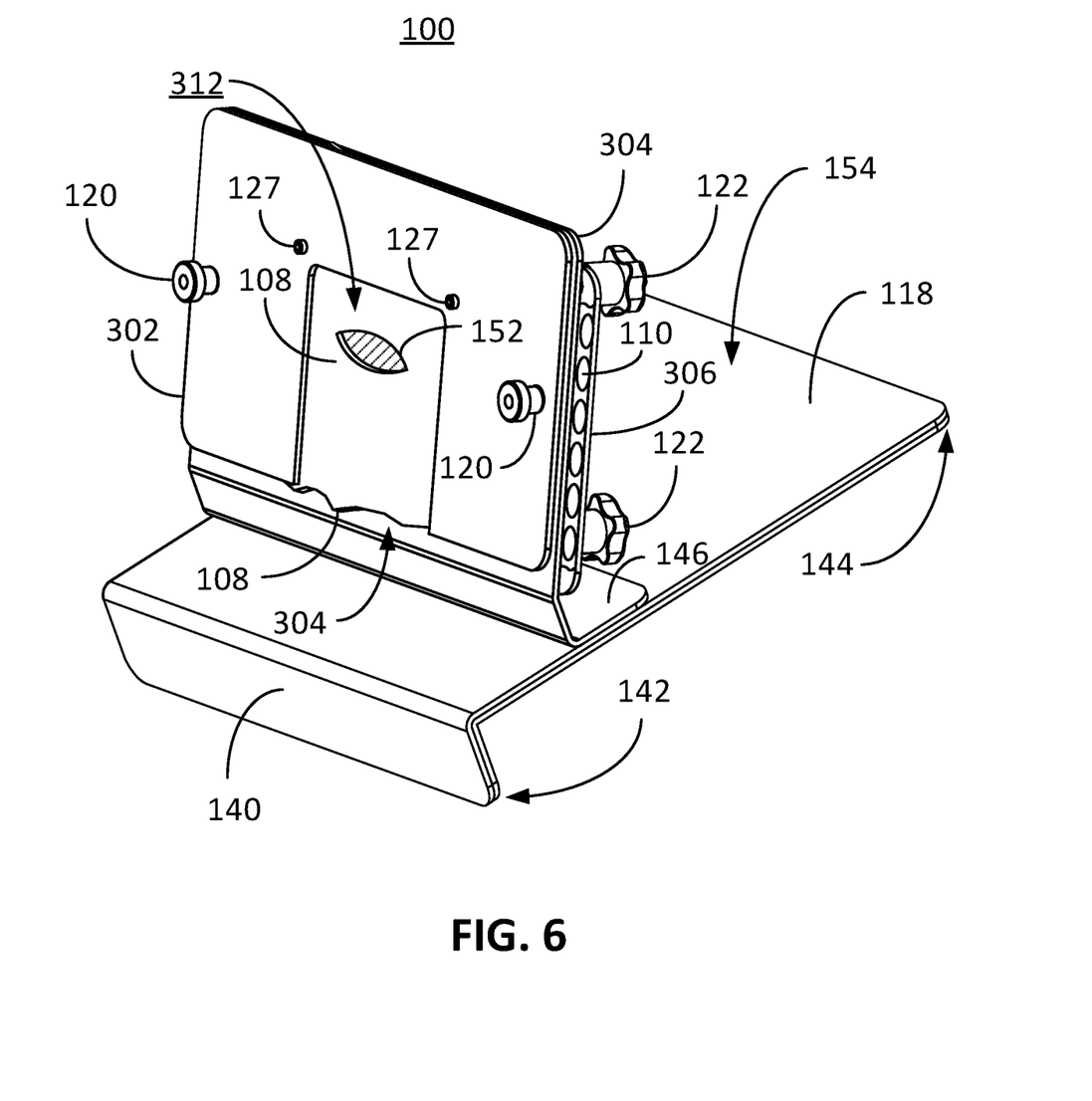
FIG. 6 illustratively depicts an isometric line drawing of a rib retention embodiment consistent with embodiments of the present invention.

FIG. 6 illustratively depicts an isometric line drawing of another embodiment of a chest tube trainer device consistent with embodiments of the present invention. In this embodiment, the essential structures are similar to that described in conjunction with FIG. 2 with the exception that at least one of the plates, in this case the front plate 302 has an aperture 312 that aperture extends to one of the sides of the plate 302 defining a notch 304. More specifically, the aperture 312 is not surrounded on all sides by the plate material, but rather forms essentially the knot notch shape 304. Certain embodiments envision all of the plates having the notch shape 304 or two of the three plates having the notch shape 304.

With the present description in mind, below are a summary of some embodiments consistent with the present invention. The elements called out below are examples provided to assist in the understanding of the present invention and should not be considered limiting.

One embodiment envisions a chest tube trainer device 100 comprising: a first plate 102 with a first aperture 112 in the first plate 102; a second plate 104 with the second aperture 114 and the second plate 104; a third plate 106 with a third aperture 116 in the third plate 106; a synthetic sheet of human-like skin 108 clamped between the first plate 102 and the second plate 104, the synthetic sheet 108 covering the first aperture 112 and the second aperture 114, the first aperture 112 and the second aperture 114 overlap; and a portion of a processed animal rib cage 110 clamped between the second plate 104 and the third plate 106, the portion 110 comprising at least two animal ribs that are adjacent to one another (e.g., part of rib #4 and rib #5 connected through muscle and tissue, or part of rib #7 and rib #8 connected through muscle and tissue, or part of rib #2, rib #3, rib #4 and rib #5), the second aperture 114 and the third 116 aperture overlap.

The chest tube trainer device embodiment 100 further imagining wherein the processed animal rib cage 100 is devoid of animal skin.

The chest tube trainer device embodiment 100 further contemplating wherein the first aperture 112, the second aperture 114, and the third aperture 116 are the same shape and size and are essentially superimposed.

The chest tube trainer device embodiment 100 further considering wherein at least one of the apertures112, 114, 116 in at least one of the plates 102, 104 or 106 is not surrounded on all sides by the plate, but rather forms essentially a notch shape 304 in the at least one of the plates 102, 104 or 106.

The chest tube trainer device embodiment 100 further envisioning wherein the first plate 102, the second plate 104, and the third plate 106 are clamped together via a plurality of cooperating nuts 120, 122 and bolts 121, 123.

The chest tube trainer device embodiment 100 further imaging wherein the first plate 102 possesses at least one slot 127 and/or pin 126 adapted to mate with the second plate 104 via a respective opposing pin 126 and or slot 127, the at least one pin 126 and slot 127 configured to retain the synthetic sheet 108 in an immobile relationship when the synthetic sheet 108 is clamped between the first plate 102 and the second plate 104, the at least one slot 127 in the at least one pin 126 in contact with the synthetic sheet of human-like skin 108.

The chest tube trainer device embodiment 100 further contemplating wherein the synthetic sheet of human-like skin 108 is in contact with the processed animal rib cage 110.

The chest tube trainer device embodiment 100 further comprising a platform 119 that holds the clamped together plates 102, 104 and 106 at an angle greater than horizontal when the platform 119 is referenced on a horizontal plane.

Another embodiment contemplates a rib retention training apparatus 100 comprising: a first plate 102 with a first aperture 112 in the first plate 102; a second plate 106 with the second aperture 116 in the second plate 106; a clamping means adapted to clamped the first plate 102 to the second plate 106 with the first aperture 112 and the second aperture 116 overlapping, a means for retaining a synthetic sheet of human-like skin 108 in a fixed position over the first aperture 112, the first plate 102 and the second plate 106 configured to compress and fixedly retain a portion of an animal rib cage 110 when the first plate 102 and the second plate 106 are clamped together, the portion covering the first aperture 112 and the second aperture 116.

The rib retention training apparatus embodiment 100 further comprising a third plate 104 with a third aperture 114 in the third plate 104, the third plate 104 disposed between the first plate 102 and the second plate 106, the third aperture 114 overlapping the first aperture 112 and the second aperture 116, the portion of the animal rib cage 110 configured to be clamped between the second plate 106 and the third plate 104, and the synthetic sheet of human-like skin 108 configured to be clamped between the third plate 104 and the first plate 102. The synthetic sheet of human-like skin 108 can be further configured to be in contact with the portion of the animal rib cage 110.

The rib retention training apparatus embodiment 100 further comprising a platform 119 that holds the clamped together plates 102 and 106 at an angle greater than horizontal when the platform 119 is referenced on a horizontal plane.

The rib retention training apparatus embodiment 100 further contemplating wherein the means for retaining is configured to stretch the synthetic sheet of human-like skin 108 taut over the first aperture 112.

The rib retention training apparatus embodiment 100 further comprising a spacer 154 that maintains a distance from the second aperture 116 to a surface 212 on which the rib retention training apparatus 100 is disposed.

The rib retention training apparatus embodiment 100 further considering wherein at least one of the apertures 112 in at least one of the plates 102 is not surrounded on all sides by the plate, but rather forms essentially a notch shape 304 in the at least one of the plates 102.

Yet another embodiment contemplates a method for assembling a rib retention training apparatus 100, the method comprising: providing a first frame 102 with a first aperture 112 in the first frame 102, a second frame 104 with a second aperture 114 in the second frame 104, and a third frame 106 with a third aperture 116 in the third frame 106; disposing a portion of an animal rib cage 110 between the second frame 104 and the third frame 106 and disposing a synthetic sheet of human-like skin 108 between the second frame 104 and the first frame 102, the portion of an animal rib cage 110 essentially covering the third aperture 116 and the synthetic sheet of human-like skin 108 essentially covering the second aperture 114, the apertures 112, 114 and 116 essentially overlapping; clamping the first frame 102, the second frame 104 and the third frame 106 together to compress the synthetic sheet of human-like skin 108 and the portion of the portion of the animal rib cage 110 in an immobile arrangement between the frames 102, 104 and 106 wherein there is at least a 2 inch distance between the third frame 106 and any surface 119 opposing the third frame 106 on the opposite side 107B of third frame 106 where the portion of the portion of the animal rib cage 110 is.

The method for assembling a rib retention training apparatus 100 further envisioning wherein the frames 102, 104 and 106 interface one another with flat surfaces.

The method for assembling a rib retention training apparatus 100 further preventing the synthetic sheet of human-like skin 108 from slipping from between the first frame 112 and the second frame 114 by mechanically locking the synthetic sheet of human-like skin 108 between the first frame 102 and the second frame 104. The synthetic sheet of human-like skin 108 can further be mechanically locked in place via a plurality of retention fixtures 126 and 127.

The method for assembling a rib retention training apparatus 100 further considering wherein the apertures 112, 114 and 116 are essentially sized equally, are essentially in the center of each respective plate 102, 104 and 106, and are superimposed during the clamping step.

The method for assembling a rib retention training apparatus 100 further providing a stand 118 that holds the clamped together plates 102, 104 and 106 at an angle greater than horizontal when the stand 118 is resting on a horizontal surface 212.

The method for assembling a rib retention training apparatus 100 further resting the rib retention training apparatus 100 on a flat surface 119 with the third aperture 116 closest to the flat surface 119, the third aperture comprising a spacer 154 providing a distance between the third aperture 116 and the flat surface 119.

The above embodiments are not intended to be limiting to the scope of the invention whatsoever because many more embodiments are easily conceived within the teachings and scope of the instant specification. Moreover, the corresponding elements in the above example should not be considered limiting.

It is to be understood that even though numerous characteristics and advantages of various embodiments of the present invention have been set forth in the foregoing description, together with the details of the structure and function of various embodiments of the invention, this disclosure is illustrative only, and changes may be made in detail, especially in matters of structure and arrangement of parts within the principles of the present invention to the full extent indicated by the broad general meaning of the terms in which the appended claims are expressed. For example, though the embodiments teach a rectangular shaped aperture creating a passageway in the three framed plates 102, 104 and 106, other aperture (opening) shapes such as, circular, elliptical, etc. could equally be used while still maintaining substantially the same functionality without departing from the scope and spirit of the present invention. Other embodiments envision needles or pointy spikes arranged to penetrate into the synthetic human-like skin 108 and/or the portion of the animal rib cage 110 instead of the pin/slot arrangement depicted. Yet other embodiments envision different kinds of clamping systems other than knurled nuts and finger nuts that compress the plates together when screwed into captured bolts. Further, the terms "one" is synonymous with "a", which may be a first of a plurality.

It will be clear that the present invention is well adapted to attain the ends and advantages mentioned as well as those inherent therein. While presently preferred embodiments have been described for purposes of this disclosure, numerous changes may be made which readily suggest themselves to those skilled in the art and which are encompassed in the spirit of the invention disclosed and as defined in the claims.

What is claimed is:

1. A chest tube trainer device comprising:
    a first plate with a first aperture in the first plate;
    a second plate with a second aperture in the second plate;
    a third plate with a third aperture in the third plate;
    a synthetic sheet of human-like skin clamped between the first plate and the second plate,
    the synthetic sheet of human-like skin covering the first aperture and the second aperture, wherein the first aperture and the second aperture overlap; and
    a portion of a processed animal rib cage clamped between the second plate and the third plate, the portion comprising at least two animal ribs, wherein the second aperture and the third aperture overlap.

2. The chest tube trainer device of claim 1 wherein the processed animal rib cage is devoid of animal skin.

3. The chest tube trainer device of claim 1 wherein the first aperture, the second aperture, and the third aperture are the same shape and size and essentially are superimposed.

4. The chest tube trainer device of claim 1 wherein the first plate, the second plate, and the third plate are clamped together via a plurality of bolts.

5. The chest tube trainer device of claim 1 wherein the first plate possesses at least one slot and/or pin adapted to mate with the second plate via a respective opposing pin and or slot, the at least one pin and slot configured to retain the synthetic sheet of human-like skin in an immobile relationship when the synthetic sheet of human-like skin is clamped between the first plate and the second plate, the at least one slot in the at least one pin in contact with the synthetic sheet of human-like skin.

6. The chest tube retaining device of claim 1 wherein the human-like skin is in contact with the processed animal rib cage.

7. The chest tube retaining device of claim 1 further comprising a platform that holds the clamped together plates at an angle greater than horizontal when the platform is referenced on a horizontal plane.

8. A rib retention training apparatus comprising:
    a first plate with a first aperture in the first plate;
    a second plate with a second aperture in the second plate;
    a clamping means adapted to clamp the first plate to the second plate with the first aperture and the second aperture overlapping,
    a means for retaining a synthetic sheet of human-like skin in a fixed position over the first aperture, the first plate and the second plate configured to compress and fixedly retain a portion of an animal rib cage when the first plate and the second plate are clamped together, the portion covering the first and the second aperture.

9. The rib retention training apparatus of claim 8 further comprising a third plate with a third aperture in the third plate, the third plate disposed between the first plate and the second plate, the third aperture overlapping the first aperture and the second aperture, the portion of the animal rib cage configured to be clamped between the second plate and the third plate, and the synthetic sheet of human-like skin configured to be clamped between the third plate and the first plate.

10. The rib retention training apparatus of claim 9 wherein the synthetic sheet of human-like skin is configured to be in contact with the portion of the animal rib cage.

11. The rib retention training apparatus of claim 8 further comprising a platform that holds the clamped together plates at an angle greater than horizontal when the platform is referenced on a horizontal plane.

12. The rib retention training apparatus of claim 8 wherein the means for retaining is configured to stretch the synthetic sheet of human-like skin taut over the first aperture.

13. The rib retention training apparatus of claim 8 further comprising a spacer that maintains a distance from the second aperture to a surface on which the rib retention training apparatus is disposed.

14. A method for assembling a rib retention training apparatus, the method comprising:
    providing a first frame with a first aperture in the first frame, a second frame with a second aperture in the second frame, and a third frame with a third aperture in the third frame;
    disposing a portion of an animal rib cage between the second frame and the third frame and disposing a synthetic sheet of human-like skin between the second frame and the first frame, the portion of a portion of an animal rib cage essentially covering the third aperture and the synthetic sheet of human-like skin essentially covering the second aperture, the apertures essentially overlapping;
    clamping the first frame and the third frame together to compress the synthetic sheet of humanlike skin, the second frame and the portion of the animal rib cage in an immobile arrangement, there is at least 2 inches between the third frame and any surface opposing the third frame that is not in contact with the portion of the animal rib cage.

15. The method of claim 14 wherein the frames interface one another with flat surfaces.

16. The method of claim 14 further preventing the synthetic sheet of human-like skin from slipping from between the first frame and the second frame by mechanically locking the synthetic sheet of human-like skin between the first frame and the second frame.

17. The method of claim 16 wherein the synthetic sheet of human-like skin is mechanically locked in place via a plurality of retention fixtures.

18. The method of claim 14 wherein the apertures are essentially sized equally, are essentially in the center of each respective plate, and are superimposed during the clamping step.

19. The method of claim 14 further providing a stand that holds the clamped together plates at an angle greater than horizontal when the stand is resting on a horizontal surface.

20. The method of claim 14 further resting the rib retention training apparatus on a flat surface with the third aperture closest to the flat surface, the third aperture comprising a spacer providing a distance of at least two inches between the second aperture and the flat surface.

* * * * *